US008177835B2

(12) United States Patent
Noettling et al.

(10) Patent No.: US 8,177,835 B2
(45) Date of Patent: May 15, 2012

(54) METHOD OF IMAGING FOR HEART VALVE IMPLANT PROCEDURE

(75) Inventors: Alois Noettling, Pottenstein (DE); Jan Boese, Eckental (DE); Matthias John, Nuremberg (DE); Volkmar Falk, Zurich (CH); Thomas Walther, Leipzig (DE)

(73) Assignee: Siemens Aktiengesellschaft, Munich (DE)

( * ) Notice: Subject to any disclaimer, the term of this patent is extended or adjusted under 35 U.S.C. 154(b) by 341 days.

(21) Appl. No.: 12/545,435

(22) Filed: Aug. 21, 2009

(65) Prior Publication Data

US 2011/0046725 A1    Feb. 24, 2011

(51) Int. Cl.
*A61F 2/24*    (2006.01)
*A61B 5/05*    (2006.01)

(52) U.S. Cl. .......................................... 623/2.1; 600/415
(58) Field of Classification Search .................. 606/130; 600/415, 416, 419, 420; 623/2.1, 2.11
See application file for complete search history.

(56) References Cited

U.S. PATENT DOCUMENTS

| 4,819,751 | A |  | 4/1989 | Shimada | |
|---|---|---|---|---|---|
| 6,368,285 | B1 | * | 4/2002 | Osadchy et al. | 606/130 |
| 6,442,415 | B1 | * | 8/2002 | Bis et al. | 600/420 |
| 7,435,257 | B2 | * | 10/2008 | Lashinski et al. | 623/2.11 |
| 7,803,168 | B2 | * | 9/2010 | Gifford et al. | 623/2.11 |
| 2006/0074485 | A1 |  | 4/2006 | Realyvasquez | |
| 2007/0030945 | A1 |  | 2/2007 | Boese | |

FOREIGN PATENT DOCUMENTS

| DE | 10 2005 012 700 | 9/2006 |
|---|---|---|
| WO | WO 2004/103223 | 12/2004 |

OTHER PUBLICATIONS

Feldman, "Percutaneous Valve Therapies: Where We Are and Where We Are Going", Complex Coronary Intervention (2006).
Dieter, "Percutaneous Valve Repair: Update on Mitral Regurgitation and Endovascular Approaches to the Mitral Valve", Applications in Imaging—Cardiac Interventions (2003), pp. 11-14.

* cited by examiner

*Primary Examiner* — Julian Woo
(74) *Attorney, Agent, or Firm* — Schiff Hardin LLP

(57) ABSTRACT

A method as a workflow for imaging for a heart valve implant procedure includes positioning the patient and an articulated imaging apparatus relative to one another, inducing rapid ventricular pacing in the patient, and imaging a region of the patient's heart to obtain image date for a three-dimensional image. The three-dimensional data is used to construct a three-dimensional image of the region of the patient's heart an the three-dimensional image is displayed for use in the implanting of the replacement heart valve. Optional steps may include obtaining a real time two-dimensional image of the patient's heart and superimposing the real time two-dimensional image with the constructed three dimensional image. The replacement valve is moved into position in the patient's heart during rapid ventricular pacing and breath hold using the superimposed two-dimensional and three-dimensional image information.

15 Claims, 3 Drawing Sheets

METHOD OF IMAGING FOR HEART VALVE IMPLANT PROCEDURE

BACKGROUND OF THE INVENTION

1. Field of the Invention

The present invention relates generally to a method of imaging a patient's heart for implant of an artificial heart valve into the heart, and in particular to a method of medical imaging as part of a heart valve implant procedure.

2. Description of the Related Art

The reduction of the pumping power of one or both heart chambers is generally referred to as a cardiac insufficiency. Cardiac insufficiency is not an actual illness, but rather is the result of various diseases and/or pathology symptoms. As a result of cardiac insufficiency, the body and its organs do not receive the necessary amount of blood per unit of time. The vital organs are supplied with only an insufficient quantity of oxygen and nutrients. Among the most important causes of cardiac insufficiency are illness of the coronary vessels (often the cause of extended infarctions), hypertension that is insufficiently medically regulated, heart muscle illness, heart muscle infection (myocarditis), illness of the pericardium, and illness of the heart valves. Illnesses of the heart valves are among the most important causes of cardiac insufficiency.

Congenital stenoses of one or more heart valves, or stenoses caused by other sources, such as, for example, calcium deposits, are frequent pathological conditions of the heart valves. In the case of a pulmonary valve stenosis, the leaflets of the pulmonary valve are thickened, so that the opening of the valve is hindered. The right chamber therefore works against an increased resistance, and forms more muscle mass, i.e. it becomes hypertrophic. In aortic valve stenosis, a narrowing or constriction of the discharge path of the left chamber occurs. The cause is a thickening of the valvular cusp and/or an underdevelopment of the aortic root. The constriction may be below the valve (sub-valvular), at the valve (valvular) or above the valve (supra-valvular). The left chamber works against an increased resistance and becomes thicker (becomes hypertrophic). Sub-valvular and supra-valvular aortic stenoses can generally be treated using balloon catheters. Mitral stenosis is normally an acquired valve defect, and is almost always the result of rheumatic endocarditis. The heart valves can be damaged by other illnesses, for example by inflammation, influenza or cardiac infarction, to the extent that the valve must be replaced or surgically modeled.

Various types of interventional surgical procedures are known for addressing one or more of the above causes of cardiac insufficiency. Until recently, a replacement of a heart valve required an open heart procedure. Mechanical or biological heart valve prostheses were implanted (to address issues with the aortic valve or pulmonary valve) or the existing valve opening was surgically shaped (to address issues with the mitral valve and tricuspid valve). Such procedures were associated with high risks and long recovery times or convalescence (up to six weeks or more) for the patient.

More recently, methods have been developed to treat heart valve stenoses in a minimally-invasive manner by the use of specially designed catheters. In principle, all four heart valves are accessible for a balloon dilation (referred to as valvuloplasty), but dilation of the tricuspid valve is only rarely implemented, due to the relative rarity of tricuspid stenosis.

The basic steps of a number of known balloon dilation procedures are described below. For balloon dilation in the case of pulmonary valve stenosis, after probing of the right or left pulmonary artery from the groin with an open-ended catheter, a relatively rigid guide wire is introduced. A special dilation catheter (referred to as a valvuloplasty catheter) can be advanced via this guide wire after the catheter has been retracted. This procedure is implemented under anesthesia, since filling of the balloon leads to a temporary interruption of circulation. In the case of less thickened valves, an excellent result with less residual resistance, and no or minimal insufficiency of the pulmonary valve, is achieved. In the case of a valve atresia, the targeted perforation of the valves by means of HF (High Frequency) energy and subsequent balloon dilation is frequently possible.

Balloon dilation in the case of aortic valve stenosis resembles the procedure for balloon dilation in the case of pulmonary valve stenosis, in that a balloon catheter is advanced via a guide wire to the location of the valve. Generally, the probing is implemented in a retrograde manner, since the left ventricle is accessible via the stenotic aortic valve.

For balloon dilation in the case of mitral stenosis, the balloon catheter can be inserted into the mitral valve either in an antegrade manner from the left atrium (after transeptal puncture) or in a retrograde manner from the left ventricle. More recently, the antegrade procedure has prevailed. The size (or area) of the opening (or aperture) of the mitral valve can be doubled, for example, by means of balloon dilation.

A catheter suitable for this purpose is described in U.S. Pat. No. 4,819,751. Such catheters have the advantage of allowing a minimally-invasive cardiac procedure to be conducted through use of the catheter.

Replacement or modeling of heart valves in a minimally-invasive manner by the use of special catheters has been tested. Integration of an artificial heart valve into a stent that is placed in the aortic valve and the pulmonary valve with a catheter is described, for example, in the Internet website www.corevalve.com or at or www.edwards.com. A detailed description can also be found in the article "Percutaneous Valve Therapies: Where We Are and Where We Are Going," by Feldman (available through the Internet site www.tct-.com). A suitable heart valve for this purpose is described in United States Patent Application Publication No. US 2006/0074485 A1.

The shape of the mitral valve and/or the valve opening thereof can be modeled with catheter-based tools, for example with the commercially available Carillon Mitral Contour System, available from the Internet site www.cardiacdimension.com. This catheter is conducted through the coronary sinus, and the procedure is known as percutaneous mitral annuloplasty.

A detailed description of known methods for repairing mitral valves can be found in the article "Percutaneous Valve Repair: Update on. Mitral Regurgitation and Endovascular Approaches to the Mitral Valve," by Dieter.

A catheter device for insertion in an annuloplasty ring is described in PCT Published Patent Application WO 2004/103233.

In contrast to the above-described diseases, diseases of the tricuspid valve are rare, but when found to exist, can be treated in procedures similar to those described above concerning the mitral valve.

Imaging for these procedures could be improved by the use of a C-arm x-ray device, such as the DynaCT C-arm imaging system available from Siemens Medical Solutions. With this device, 2D (two-dimensional) projection images as well as 3D (three-dimensional) soft tissue images, typically obtained after the injection of a contrast agent, of a beating heart can be produced. A method and apparatus for conducting an interventional procedure involving heart valves using a robot-based X-ray device is disclosed on co-pending U.S. patent application Ser. No. 12/046,727, filed on Mar. 12, 2008. A multi-axis articulated robot suitable for use in the inventive method and apparatus is described in DE 10 2005 012 700 A1, the teachings of which are incorporated herein by reference. Moreover, a procedure is described in United States Patent Application Publication No. 2007/0030945 wherein a 3D representation of the relevant anatomy of a heart, in particular soft tissue images, ensues with the use of ECG gating, the teachings of which are incorporated herein by reference.

Interventional aortic valve implantation is a new method of minimally-invasive surgery, by which an open operation can be avoided. One problem with the aortic valve implantation is the risk of complications. In particular in the positioning of the artificial aortic valves, a precise knowledge of the anatomy (for example position of the coronary ostia, diameter of the aortic annulus etc. is necessary in order to avoid complications. An additional problem is the high level of contrast agent that is used.

The procedure was previously supported via pre-operative computer tomography (CT), in particular for measuring the anatomical parameters. Relatively large quantities of contrast agent are necessary to perform such computer tomography imaging. The disadvantage of CT is that the data acquisitions are typically performed a few days before the procedure and therefore do not reproduce the exact anatomy of the relevant area of the patient that may be present during the procedure. During the procedure, conventional two-dimensional digital radiography acquisitions are repeatedly conducted with contrast agent injection. Large quantities of the contrast agent are necessary for the repeated image acquisitions. Moreover, trans-esophageal ultrasound (TEE) is used, in particular for measuring the diameter, for example, of the aortic annulus.

The positioning of the replacement aortic valve is conducted using rapid ventricular pacing (RVP) while the planning image exposures are conducted without the use of RVP.

SUMMARY OF THE INVENTION

The present invention provides a method as a workflow of a 3D image assistance for aortic valve implantation. The method for 3D imaging in the OP (or OR) or interventional laboratory is thereby central. Using an imaging system to obtain the images, imaging of relevant portions of the patient is performed by inducing a same state in the patient's heart as will be used during the following valve implant procedure, which in the preferred embodiment is rapid ventricular pacing. The resulting image data is processed to construct a three-dimensional image which will be displayed on a display apparatus for use during the implant procedure.

DETAILED DESCRIPTION OF THE PREFERRED EMBODIMENTS

Figure 1:
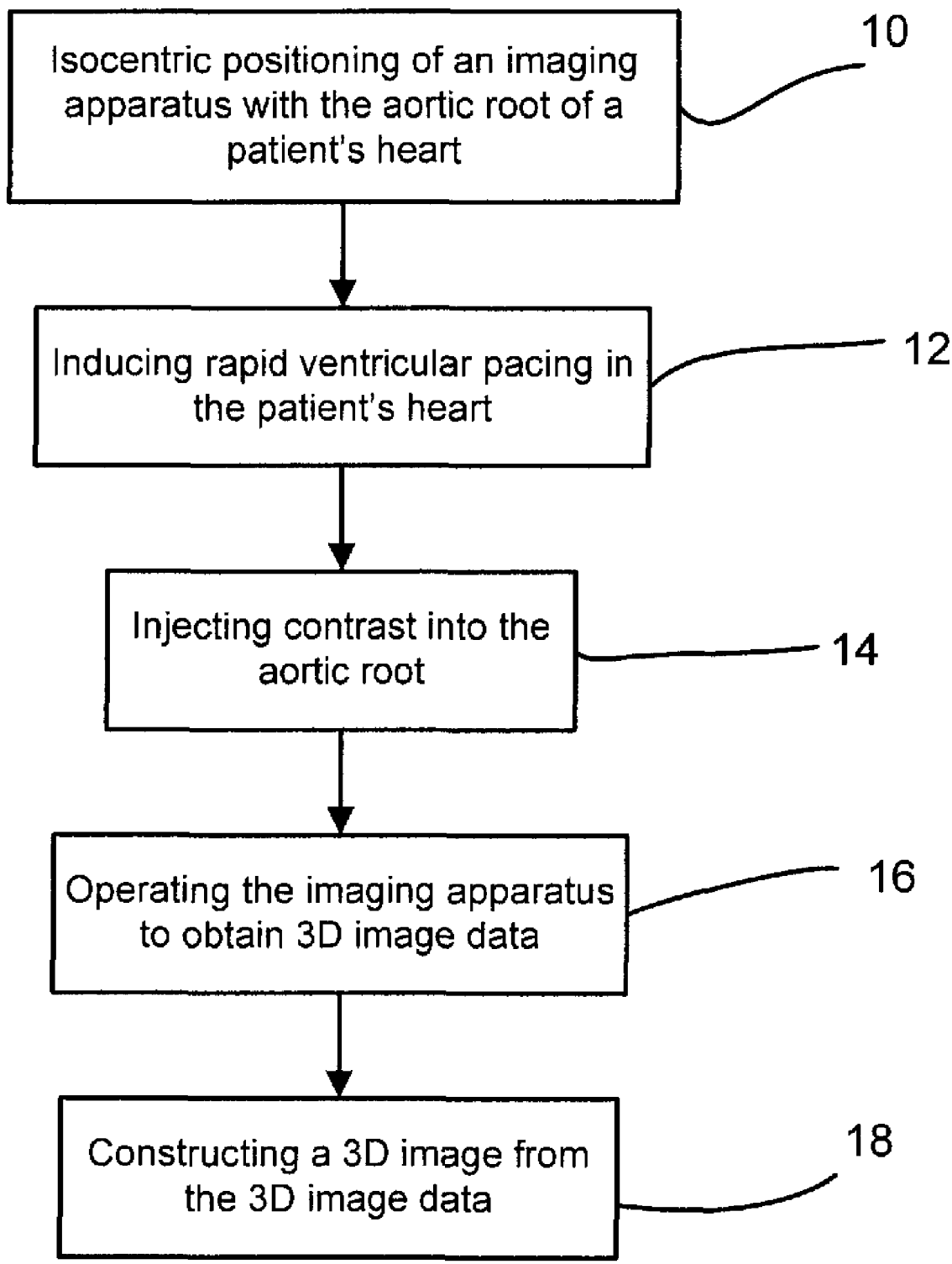
FIG. 1 is a process flow chart showing the method of imaging according to the present invention.

The invention provides a method of imaging so as to produce images to be displayed on a display device for use in an artificial heart valve implant procedure as shown in FIG. 1. The method includes the step, as shown at block 10, of isocentric positioning of the imaging system, such as the Siemens Dyna CT imaging system or other imaging system, with the aortic root of the patient's heart. The aortic root is the portion of the aorta that attaches to the heart and which contains the aortic valve.

After centering the aortic root relative to the imaging system's projection direction, rapid ventricular pacing of the patient's heart is triggered, or induced, in the patient, at step 12. The patient is also requested to hold their breath, or otherwise caused to temporarily stop breathing, such as if under control of a ventilator of the patient is under anaesthesia. The combination of rapid ventricular pacing and breath-hold reduces movement of the organs in the patient.

During the rapid ventricular pacing, a contrast agent is injected into the patient via a catheter, for example into the aortic root, at step 14. The contrast injection is preferably performed by an automatic injector. In one example, the contrast injection injects a contrast agent of 20 ml Ultravist 370, diluted to 60 ml, flow 15 ml/s over 4 second. A one second delay for the x-ray is provided to allow for distribution of the contrast agent.

With the contrast agent injected, an imaging run is performed by operation of a medical imaging apparatus, such as an articulated x-ray imaging apparatus, at step 16. In the example, an image data acquisition is performed by a Siemens DynaCT imaging apparatus. For the example, the imaging apparatus is set at 5 seconds protocol with 128 projections over 200 degrees, 0.36 µGy/p. The image data obtained during the imaging run is imaging data for constructing a three-dimensional image.

Following the image data acquisition, an image construction step is performed, at step 18. The image construction is a three dimensional reconstruction using, in the preferred embodiment, DynaCT algorithms, which are programs of Siemens AG. Examples of the algorithms include truncation correction, scattered ray correction, over-radiation correction, beam hardening correction and others. The constructed three-dimensional image from the image data may be displayed now or stored for later use or display. The display of the constructed image is performed on a display device for the physician and potentially for other medical personnel who may be involved in the valve implant procedure. The constructed image data being displayed represents the physical structures of the patient's heart and possibly surrounding tissues and organs. The imaging data has therefore been transformed.

The imaging in preparation of the aortic valve implant may now be complete, or optional additional method steps may be performed.

Figure 2:
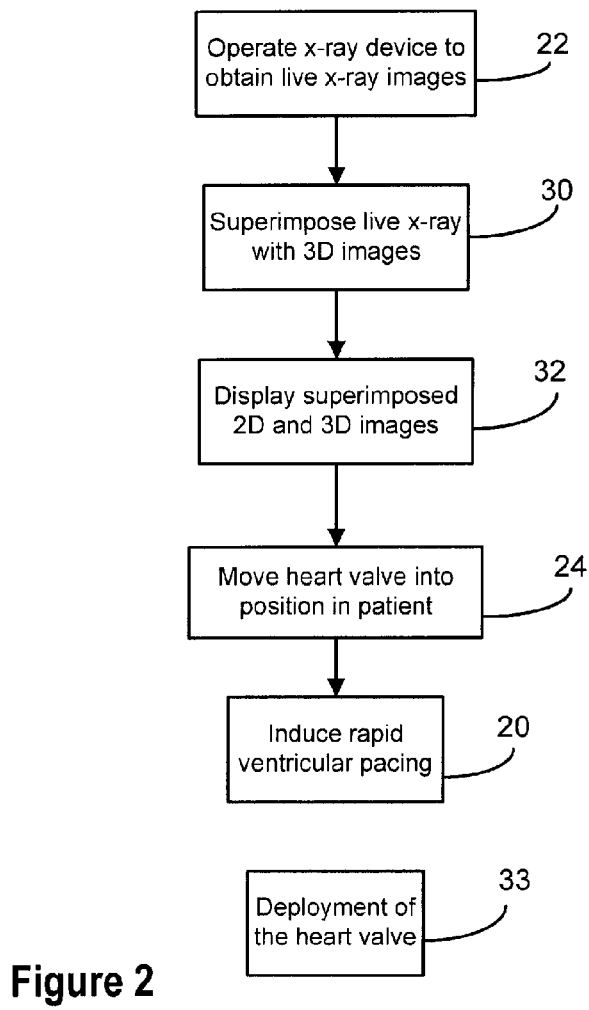
FIG. 2 is a flow chart of optional additional method steps.

The implant of the heart valve may be performed once the three-dimensional images are obtained, as shown in FIG. 2. The imaging device is operated to obtain live x-ray images of the relevant portions of the patient, at step 22. The live x-ray images and 3D images are superimposed, at step 30. The superimposed images are displayed, at step 32. The replacement heart valve is moved into position in the patient, at step 24. Rapid ventricular pacing is induced in the patient, at step 20. Thereafter, the heart valve is deployed, at step 33.

The implant is performed by minimally invasive procedures, and uses rapid ventricular pacing 20 of the patient's heart so that the same or similar conditions exist for the implant as for the imaging. Breath-hold may be used. The implant can be performed a very short time after the image acquisition, and may be performed without moving the patient. The patient may remain in the imaging suite of the medical facility during both the pre-implant procedure imaging and during the implant procedure. The patient may remain in the same position, such as on an operating/imaging table and thus is unmoved so that body tissues, organs, and the conditions thereof are unchanged between the imaging and implant procedures. The valve implant may be moved into position at step 24 in the patient using the live x-ray images of the patient obtained in step 22 and the images may be obtained, for example, using the same imaging apparatus as used for the pre-implant imaging.

Figure 3:
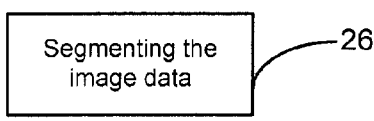
FIG. 3 is a block illustrating an optional additional method.

An optional step may be provided of segmentation of the three dimensional data of the pre-implant imaging run, as shown in FIG. 3 at 26. Either manual or automatic segmentation of the image data is performed, or segmenting may be performed by marking of relevant anatomical structures, for example by marking of the aorta, coronary ostium, or valve plane. In one example, the data is segmented by manual adjusting of the contrast and brightness levels of the displayed image on the image display device. The data may also be segmented by using the syngo InSpaceEP program (a program of Siemens AG), by using the syngo iGuide program (another program of Siemens AG), or by model-based segmentation algorithms running on the imaging system or on a general purpose computer. In the preferred embodiment, the segmentation step is performed without user interaction so that it can be executed without using additional personnel during the operation.

Figure 4:
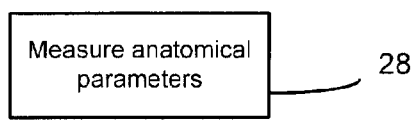
FIG. 4 is a block illustrating a further optional additional method.

A further optional step is to provide measurement of relevant anatomical parameters using the image data, as shown in FIG. 4 at 28. For example, geometric parameters (for example, diameters or spacings) of anatomical features are measured from the images or, respectively, from segmented structures of the image data. The measurements are preferably automatically determined without user interaction, for example based on models. Relevant parameters for measurement for the aortic valve implant include, for example, the diameter of the aortic annulus, the distances of the coronary ostium from the valve plane, and the position and orientation of the valve plane.

A further optional feature of the present method is superimposition of the structures with live x-ray images on the display device, as shown in FIG. 2 at step 30. The pre-implant images or, respectively, segmented structures derived from the pre-implant images are mixed into the live x-ray image by means of 2D/3D superimposition of the displayed image data at step 32. Software for performing such superimposition is known. Registration between the 3D images of the pre-implant imaging run and live x-ray images of the patient is determined from the known, calibrated geometry of the x-ray system. To avoid patient and organ movements, the deployment of the valve for implant during the superimposition of the images uses RVP (rapid ventricular pacing) of the heart (as in the 3D image acquisition steps). Both the 2D and 3D images thereby represent an approximately identical heart phase state.

Figure 8:
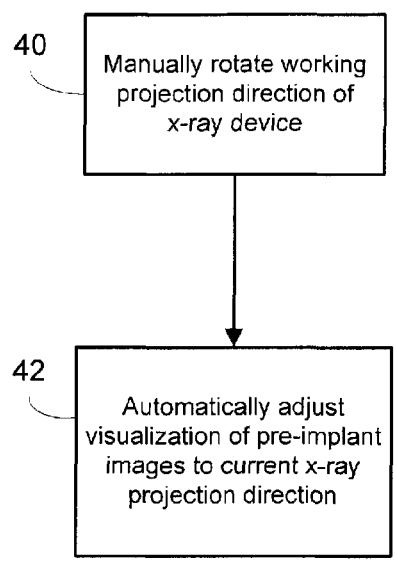
FIG. 8 is flow diagram illustrating an optional method for determining a working direction of the x-ray device.

A further optional feature of the present method is to use the pre-implant image or segmented structures to find an appropriate working projection for the x-ray imaging device. Typically, the optimum x-ray projection direction is parallel to the aortic valve plane. One way to achieve this is shown in FIG. 8 and includes step 40 of manually rotating the working projection direction of the x-ray device and step 42 of automatic adjustment of the visualization of the pre-implant images to correspond to the changes in the working projection direction of the x-ray device. Preferably, the adjustment of the visualization is performed simultaneously with the movement of the x-ray device. The pre-implant images are displayed on a display device with the visualization direction that corresponds to the current x-ray projection direction from step 40.

Figure 9:
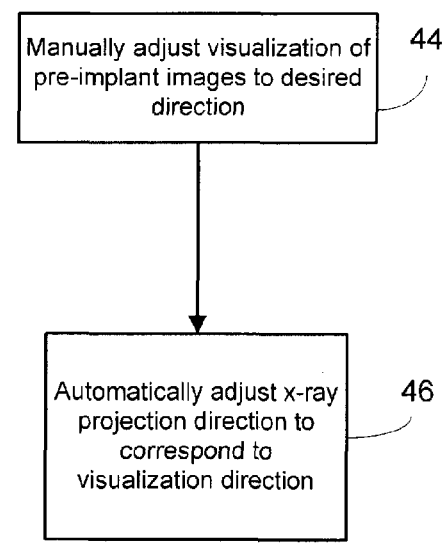
FIG. 9 is a flow diagram illustrating an alternative method to FIG. 8 for determining the working direction of the x-ray device.

Another way to find the working projection direction is shown in FIG. 9, and includes the step 44 of a medical professional manually bringing the visualization of the images on the display device into the appropriate viewing angle or direction. According to step 46, the imaging system will then adjust x-ray device automatically so that x-ray device is oriented at the same corresponding the x-ray projection direction.

Figure 5:
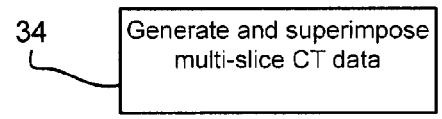
FIG. 5 is a block illustrating another optional additional method.

Yet another optional step, as shown in FIG. 5 at step 34, of the present method provides for superimposition of the structures from MSCT (multi slice computer tomography) data with live x-ray images. The CT data can exhibit a better or, respectively, more precise image quality. To superimpose these data (analogous to step 30), however, these must be registered with x-ray images. For this the (automatically registered) DynaCT image is used for indirect registration.

Figure 6:
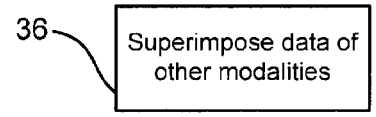
FIG. 6 is a block illustrating yet another optional additional method.
Figure 7:
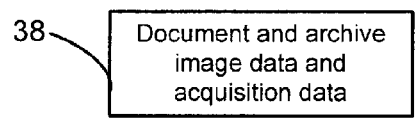
FIG. 7 is a block illustrating a step is generally performed at the conclusion of each imaging method.

A superimposition of the structures with other imaging modalities provides yet another optional feature of the method, as shown in FIG. 6 at step 36. For joint usage of various image modalities, the structures are fused with other image modalities (for example with MR (magnetic resonance), ultrasound, or CT (computed tomography) image data).

An automatic IT-based documentation of the procedure is provided. All the relevant steps, times, measurement results, generated images/structures are automatically documented and archived as, for example, image data and acquisition data. The documenting and archiving is achieved by transfer of the data to a computer readable media, such as a computer hard drive, solid state memory, magnetically and/or optically recordable tape or disc, or other storage apparatus, of a computer system. In a preferred embodiment, the data is transferred over a computer network, such as a local network or wide area network, or may be transferred via the Internet or other communication channel.

The present method provides many advantages over the prior workflow processes. For example, a distinctly smaller quantity of contrast agent is required for imaging in a Dyna CT imaging than is required for CT imaging. There is a contrast agent savings via superimposition of the structures onto 3D image data. In addition, there is a dose savings in Dyna CT imaging relative to CT imaging. Further advantages are that there is an inherent and more precise registration of Dyna CT structures with x-ray images. The workflow is optimized in the present procedure via simplified segmentation and measurement.

Testing of the present method has obtained very good images for use in an implant procedure.

Although other modifications and changes may be suggested by those skilled in the art, it is the intention of the inventors to embody within the patent warranted hereon all changes and modifications as reasonably and properly come within the scope of their contribution to the art.

We claim:

1. A method of imaging a patient for a heart valve implant procedure, comprising the steps of:
   positioning the patient relative to an articulated imaging apparatus to provide isocentric positioning of an aortic root of the patient's heart relative to the imaging apparatus;
   inducing rapid ventricular pacing in the patient;
   injecting a contrast agent into the patient during the rapid ventricular pacing state;
   imaging a region of the aortic root using the articulated imaging apparatus to obtain image data for constructing a three-dimensional image; and
   constructing a three dimensional image using data from the imaging step.

2. A method as claimed in claim 1, further comprising the step of:
   segmenting image data obtained in said imaging step.

3. A method as claimed in claim 2, wherein said segmenting step is performed automatically.

4. A method as claimed in claim 1, further comprising the step of:
   measuring anatomical parameters from the image data obtained in said imaging step.

5. A method as claimed in claim 4, wherein said measuring step is performed automatically.

6. A method as claimed in claim 1, further comprising the steps of:
   imaging the patient using an x-ray imaging apparatus to obtain two-dimensional x-ray image data of a region of the patient's heart;
   superimposing the two-dimensional x-ray image data in real time with the three-dimensional image obtained in the imaging step to obtain three-dimensional image data;
   displaying the superimposed two-dimensional and three-dimensional images on a display apparatus;
   inducing rapid ventricular pacing in the patient during the imaging to obtain two-dimensional image data so as to cause the patient's heart to be in a substantially identical heart phase state as during the imaging to obtain the three-dimensional image data;
   introducing a replacement aortic valve into position in the patient's heart during the rapid ventricular pacing using the displayed superimposed real time two-dimensional x-ray image and three-dimensional image data.

7. A method as claimed in claim 1, further comprising the steps of:
   generating a multi-slice computed tomography image from the three-dimensional image data;
   imaging the patient using an x-ray imaging apparatus to obtain two-dimensional x-ray image data of a region of the patient's heart;
   superimposing the two-dimensional x-ray image data in real time with the multi-slice computed tomography image; and
   displaying the superimposed two-dimensional and multi-slice computed tomography images on a display apparatus.

8. A method as claimed in claim 1, further comprising the steps of:
   segmenting structures of the patient within the three-dimensional image; and
   fusing the structures with a further image modality.

9. A method as claimed in claim 1, wherein said further image modality is selected from the image modalities consisting of a magnetic resonance imaging apparatus, a computed tomography imaging apparatus, and an ultrasound imaging apparatus.

10. A method as claimed in claim 1, wherein said step of injecting the contrast agent includes injecting the contrast agent into or close to the aortic root.

11. A method as claimed in claim 1, further comprising the step of:
    adjusting a projection direction of an x-ray imaging device and a visualization direction of pre-implant images to correspond with one another.

12. A method as claimed in claim 11, wherein said step of adjusting includes the steps of:
    positioning the projection direction of the x-ray imaging device, and
    automatically adjusting the visualization direction of the pre-implant images on a display to correspond to the projection direction of the x-ray imaging device.

13. A method as claimed in claim 11, wherein said step of adjusting includes the steps of:
    positioning the visualization direction of the pre-implant images; and
    automatically adjusting the projection direction of the x-ray imaging device to correspond to the visualization direction.

14. A method as claimed in claim 1, further comprising the step of:
    inducing a breath-hold by one of instructing the patient to breath-hold or stopping a ventilator if the patient is anaesthetized.

15. A method of imaging a patient for a heart valve implant procedure, comprising the steps of:
    positioning the patient relative to an imaging apparatus to provide isocentric positioning of a predetermined structure of the patient's heart relative to the imaging apparatus;
    inducing rapid ventricular pacing in the patient and instruct the patient to breath-hold;
    injecting a contrast agent into a portion of the patient's heart during the rapid ventricular pacing state;
    imaging a region of the patient's heart using the imaging apparatus to obtain image data for constructing a three-dimensional image;
    constructing a three dimensional image using data from the imaging step; and
    using the constructed three dimensional image during implant of a heart valve in the patient's heart.

* * * * *